United States Patent [19]
Shalvi

[11] Patent Number: 5,372,501
[45] Date of Patent: Dec. 13, 1994

[54] DENTAL AID

[75] Inventor: Ram Shalvi, Kwai Chung, Hong Kong

[73] Assignee: Solar Wide Industrial Ltd., Kowloon, Hong Kong

[21] Appl. No.: 743,320

[22] PCT Filed: Feb. 20, 1990

[86] PCT No.: PCT/GB90/00270

§ 371 Date: Oct. 17, 1991

§ 102(e) Date: Oct. 17, 1991

[87] PCT Pub. No.: WO90/09206

PCT Pub. Date: Aug. 23, 1990

[30] Foreign Application Priority Data

Feb. 20, 1989 [GB] United Kingdom ............ 8903784.0
Jan. 15, 1990 [GB] United Kingdom ............ 9000875.6

[51] Int. Cl.⁵ ............... A61C 3/00; A61C 19/00; A46B 9/04
[52] U.S. Cl. ............... 433/32; 15/167.1; 604/20; 132/321
[58] Field of Search ............ 132/321; 15/167.1, 167.2; 604/20; 128/393, 787; 433/32

[56] References Cited

U.S. PATENT DOCUMENTS

| | | | |
|---|---|---|---|
| 534,528 | 2/1895 | Sonn | 128/393 X |
| 2,022,457 | 11/1935 | Brown | 128/393 X |
| 2,618,801 | 11/1952 | Hibbs | 15/167.1 |
| 3,478,741 | 11/1969 | Simor | 604/20 |
| 3,520,297 | 7/1971 | Bechtold | 604/20 |
| 4,526,570 | 7/1985 | Nakagawa et al. | 604/20 |
| 4,665,921 | 5/1987 | Teranishi et al. | 128/787 X |
| 4,691,718 | 9/1987 | Sakuma et al. | 132/84 |
| 4,726,806 | 2/1988 | Hukuba | 15/167.1 X |
| 4,744,124 | 5/1988 | Wang et al. | 15/167.1 X |
| 4,780,924 | 11/1988 | Hansen et al. | 15/167.1 X |
| 4,944,296 | 7/1990 | Suyama | 604/20 X |
| 4,969,868 | 11/1990 | Wang | 128/787 X |
| 5,133,102 | 7/1992 | Sakuma | 128/393 X |

*Primary Examiner*—Paul J. Hirsch
*Assistant Examiner*—Nicholas D. Lucchesi
*Attorney, Agent, or Firm*—St. Onge Steward Johnston & Reens

[57] ABSTRACT

A toothbrush (10) for applying an electrical stimulus to the gingival region has an electrode (40) on the handle and an electrode (22) having nibs (24) at the base of the bristles (20). Electronic circuitry (28) is housed in the handle (14) for applying a bipolar voltage waveform, which is preferably a square wave of about 50 Hz, across the electrodes (22,40). A device such as an LED or buzzer is provided for indicating when the toothbrush is switched on.

13 Claims, 5 Drawing Sheets

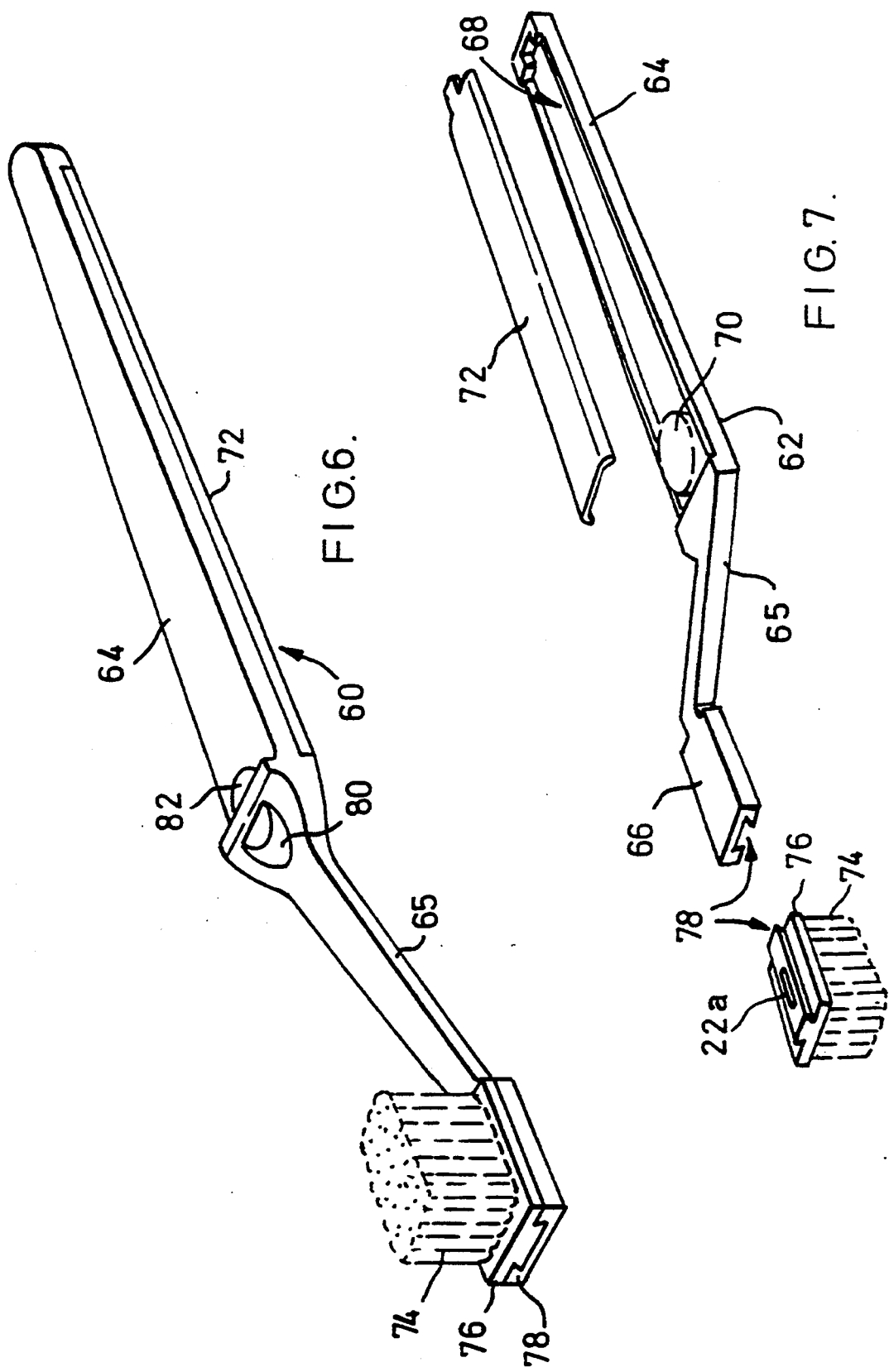

DENTAL AID

The present invention relates to a dental aid.

It is known to provide toothbrushes which include means for applying a DC current which passes from the bristles portion of the brush, through the mouth and body of the user to the handle of the brush. U.S. Pat. No. 4,691,718 describes a toothbrush with an ion-eluting ceramic head which aims to deposit flourine ions on the teeth and also help remove tartar.

Aside from the teeth themselves it is important to take care of the gums or gingival region of the mouth.

According to the present invention there is provided a dental aid arranged to apply bi-polar electrical signals to the gingival region of the mouth having a sinusoidal, square or sawtooth waveform.

The dental aid may comprise a toothbrush having a first electrode in the region of the brush for making electrical contact with the mouth of a user, and a second electrode for making electrical contact with the hand of the user. The second electrode may be mounted on a head of the tooth brush for making electrical contact with the mouth of the user.

Preferably there is no direct physical contact between the first electrode and the mouth. Bristles can be provided in the region of the first electrode, may be electrically conductive and may be electrically connected to the first electrode. Contact will normally be made through saliva, toothpaste, etc., in the mouth, and in-particular will be made with the gingival region of the mouth.

Preferably electronic circuitry for applying a voltage, normally restricted to a maximum mean value of about 3 volts, across the electrodes is housed in a body of the dental aid. A power supply, such as a Lithium cell, may also be housed in the body. The circuitry may be arranged to be powered from a mains supply via a cable and isolating transformer. Very preferably, the circuitry includes means for limiting the current flow between the electrodes. Typically, the current is limited to, say, 4 milliamps or 150 microamps.

Preferably the frequency of the bipolar signal is between about 30 and 70 $H_z$, and more particularly between about 40 and 60 $H_z$.

It has also been found that the body may be more conducive to a higher frequency signal, and so a higher frequency may also be preferred, between about 2,000 and 4,000 $H_z$, and preferably about 2,800 $H_z$. A frequency of about 60 $KH_z$ may also be used.

It is known that an electrical signal can be applied to the body at certain points to achieve a therapeutic effect. It has been found that application of the electrical signal to the mouth region, and particularly the gingival region, can improve oral hygiene, reduce cavity generation, plaque and gum disease and generally have a beneficial therapeutic effect. The fluctuating electrical signal may be effective to destroy anerobic bacteria, for example.

Means may be provided for indicating audibly or visibly to the user that the electrical signal is being applied. A timer may be incorporated to indicate that when the signal has been applied for a predetermined period; typically such a period will be about three minutes.

The dental aid may be in the form of a tooth pick, a floss holder, and a water pick, for example.

Other preferred features and advantages of the invention will be apparent from the following description and the accompanying claims.

The invention will be further described by way of example with reference to the accompanying drawings, in which:

FIG. 6 is a perspective view of a toothbrush forming second embodiment of the invention;

FIG. 7 is an exploded view of the toothbrush of FIG. 6;

Figure 1:
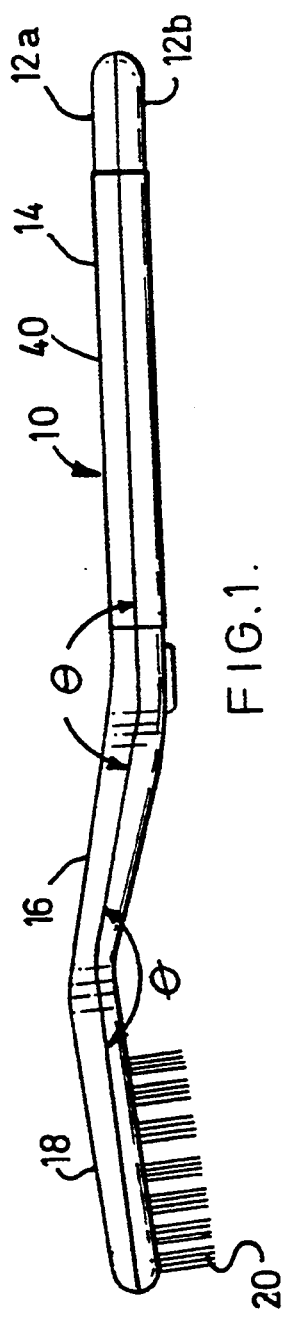
FIG. 1 is a side view of a toothbrush forming a first embodiment of the invention.

Referring to FIGS. 1 to 4, a toothbrush 10 in accordance with the invention is of generally conventional shape and comprises a plastics housing formed in two halves 12a, 12b which are welded together. The housing has a handle 14, a neck 16 and a head 18. Plastic bristles 20 are mounted in the head 18 in a conventional manner for use in brushing the teeth.

Referring to FIG. 1, it can be seen that the head 18, neck 16 and handle 14 are at an angle to each other. The neck 16 is at an angle theta to the handle 14, which is preferably between +160 and +170 degrees, and in the embodiment shown is about 165 degrees. The head 18 is at an angle phi to the neck 16, and is preferably between about −145 and −170 degrees, and in the embodiment shown is about −153 degrees, so that the head is at about −168 degrees to the handle.

Figure 2:
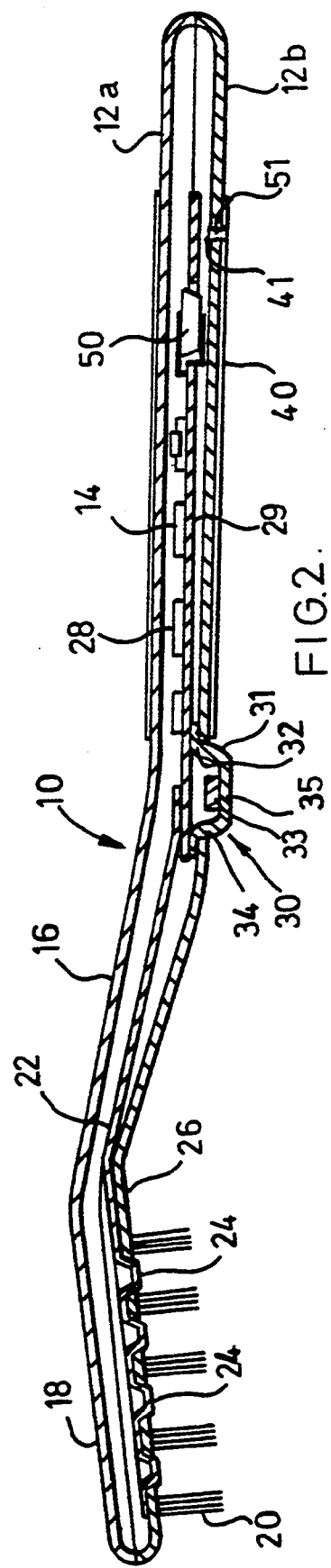
FIG. 2 is a longitudinal cross-section through the toothbrush of FIG. 1.
Figure 4:
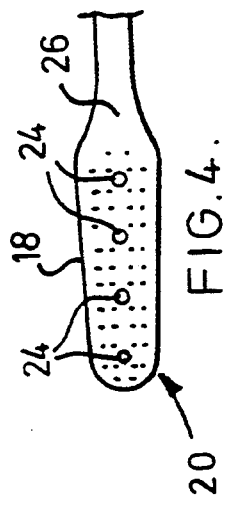
FIG. 4 is an underneath view of a head of the toothbrush of FIG. 1.
Figure 3:
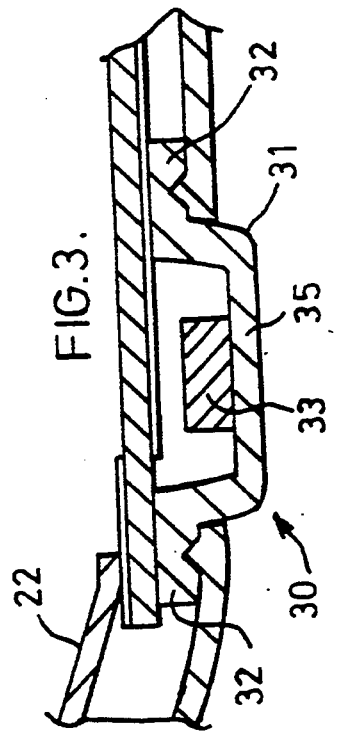
FIG. 3 is a fragmentary longitudinal cross-section through the toothbrush of FIG 1.

As seen in FIGS. 2 and 4, a first electrode 22 of stainless steel is mounted in the head 18 on the lower casing half 12b and comprises four nibs 24 which project through a bottom wall 26 of the lower casing half 12b into the region at the base of the bristles 20. The nibs 24 are just proud of the outer surface of the wall 26 and are surrounded by the bristles 20 so that they will not normally make direct contact with the teeth or other mouth parts of a user.

The first electrode 22 extends inside the housing along the neck 16 to make contact with circuitry 28 on a printed circuit board 29 which is housed in the handle 14.

A water proof switch contact is formed in the lower casing half 12b at the end of the handle 14 near the neck 16. The switch contact 30 comprises a flexible non-conductive silicon rubber cone having a circular wall 31 having a flange 32 which is sandwiched between the lower casing wall 12b and the circuit board 29 to form a water tight seal. A conductive pad 33 is glued to the inside of a flat wall 35 of the cone and is arranged to bridge two contacts 36, 37 (FIG. 5) on the printed circuit board 29 when the wall 35 is pressed by, say, the thumb of a user.

A second electrode 40 is electroplated on the outside surface of the casing 12 in the region of the handle 14 to make contact with the hand when the toothbrush is held normally. The electrode 40 is electrically connected to a printed circuit spring 41 which connects with a through connector 51 to the electroplated electrode 40.

The electrode 40 can be provided by other means. For example, the electrode 40 may consist of a piece of stainless steel on the casing 12.

Figure 5:
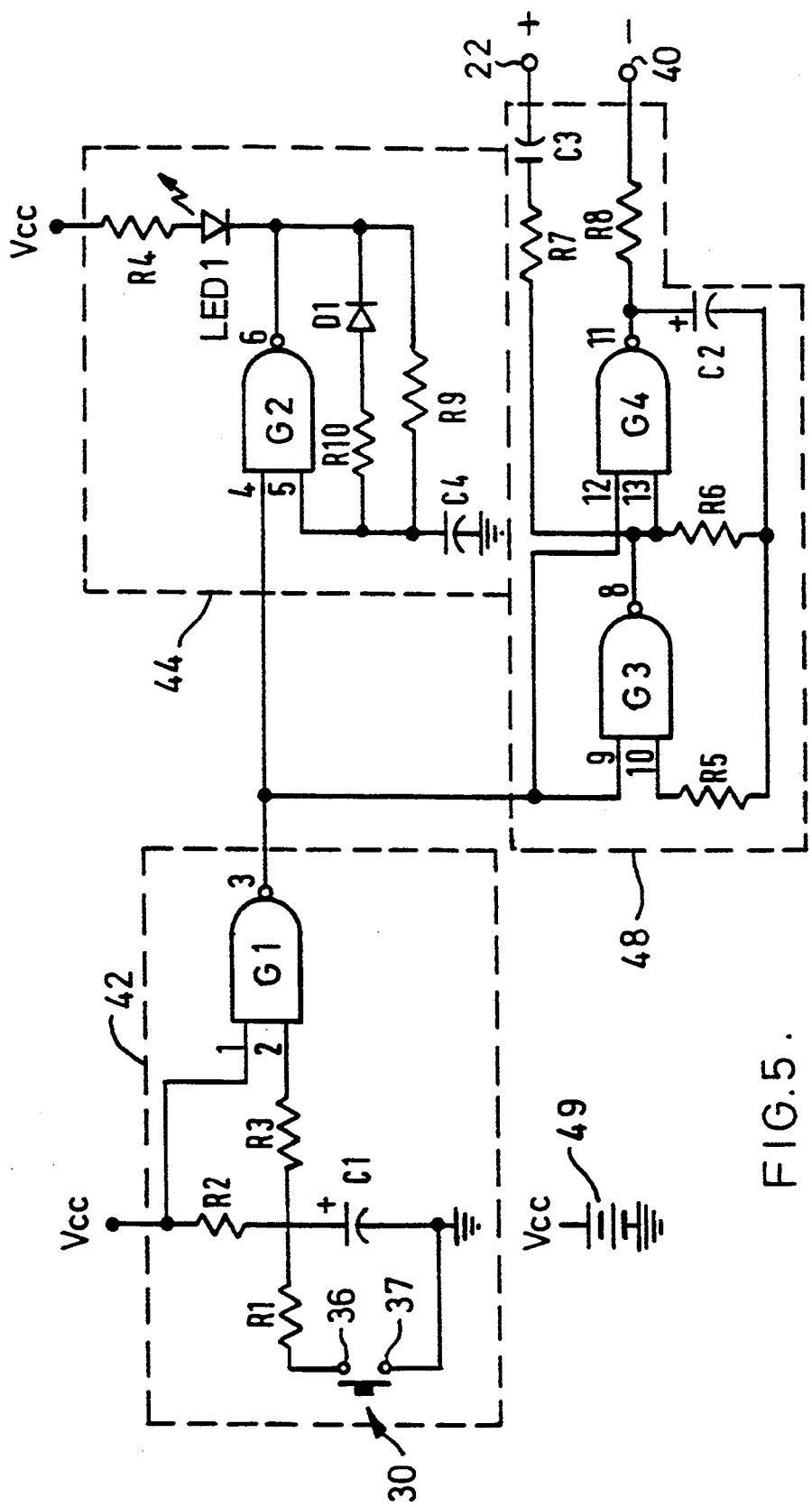
FIG. 5 is a diagram of circuitry housed in the toothbrush of FIG. 1.

FIG. 5 shows circuitry which is housed in the housing 12, mounted on the circuit board 29. The circuitry comprises a timer 42, an indicator circuit 44, and an oscillator and waveform generator 48, and is powered by a 3 volt lithium cell 49.

The timer circuit 42 comprises a schmitt trigger NAND gate G1 having one input connected to the logic voltage supply Vcc, and its second input connected to earth via a capacitor C1 and to the logic voltage supply Vcc via resistor R2. Switch 30 is normally open. At start-up conditions, the inputs 1 and 2 to gate G1 are both high and hence the output 3 is low. When switch 30 is closed momentarily, the capacitor C1 is discharged rapidly and input 2 goes low, hence the output 3 goes high to turn on the indicator circuit 44 and oscillator 48. When switch 30 is released (opened) the capacitor C1 is charged via resistor R2. After a time T which is dependent on the values of R2 and C1, input 2 goes high and hence output 3 goes low, switching off the indicator circuit 44 and oscillator 48. In one preferred embodiment resistor R2 and capacitor C1 are selected so that the output 3 remains high for a period of between about 20 and 40 seconds and particularly about 30 seconds. In another preferred embodiment the time period is about 3 minutes. If during this period switch 30 is closed again, capacitor C1 will be discharged again and hence the period of, say, 30 seconds will start afresh from the moment when switch 30 is opened. Resistors R1 and R3 are for circuit protection.

The indicator circuit 44 comprises a light emitting diode LED1 controlled by a NAND gate G2. A first input 4 of gate G2 is connected to the output 3 of gate G1 and the second input 5 is connected to earth via a capacitor C4, and to the output 6 of the gate G2 via a resistor R10 and diode D1 connected in parallel with a resistor R9. The cathode of LED1 is connected to the output 6 of gate G2. At start-up, output 3 and hence input 4 are low but both will go high when the capacitor C1 is rapidly discharged by closing switch 30, and will remain at high until the time period T provided by the timer 42 expires. During the time period T, input 5 and output 6 of gate G2 will remain at opposite logic levels. When input 5 is low and output 6 is high, capacitor C4 is charged via resistor R9. The voltage of capacitor C4 will eventually cause input 5 to go high, and will thereby cause output 6 to go low. Under this condition, capacitor C4 will be discharged via resistors R9 and R10, until input 5 goes low and hence output 6 goes high. LED1 will light up when output 6 is low, and will be switched off when output 6 is high. Resistor R4 serves to limit current passing through LED1.

The capacitor C4 charging time (controlled by R9) is longer than the discharging time (R9 and R10 in parallel) and hence LED1 is off for longer periods than it is on to conserve power.

In place of, or in addition to the LED1 a buzzer may be driven by the indicator circuit 44. It has been found important that the user be given an indication that the toothbrush is "working".

The waveform generator 48 is an astable multivibrator comprising two NAND gates G3, G4. Each gate has an input 9, 12 connected to the output 3 of gate G1. Output 11 of gate G4 is connected via a capacitor C2 and respective resistors R6, R5 to the input 13 of gate G4 and 10 of gate G3. The first, "positive" electrode 22 is connected to output 8 and input 13 and the second, negative electrode 40 is connected to output 11.

During the time period T provided by the timer 42, both inputs 9 and 12 of gates G3 and G4 remain at high, causing the other input 10, 13 and the output 8, 11 of each gate G3, G4 to remain at opposite logic levels with respect to each other. When capacitor C2 is discharged and then subsequently charged in the direction from input 13 to output 11 of gate G4, it will eventually cause input 10 of gate G3 to go high, thus reversing the direction of discharging or charging of capacitor C2. Whereupon, when the capacitor C2 is discharged and subsequently charged in the opposite direction from output 11 to input 13 of gate G4, it will eventually cause input 10 of gate G3 to go low, thus reversing again the direction of charging or discharging of capacitor C2. The cycle repeats at the desired frequency. A first preferred frequency range is from 30 to 70 $H_z$, and more particularly from 40 to 60 $H_z$, particularly about 50 $H_z$.

It has been found that the body may be more receptive to a higher frequency range, and another preferred embodiment of the invention provides a signal in the frequency range 2,000 to 4,000 $H_z$, and more preferably about 2,800 $H_z$. In some applications it has been found advantageous to use much higher frequencies, say about 60 $KH_z$.

The output signal at electrodes 22, 40 is therefore a bipolar square waveform. The maximum instaneous output current is preferably limited to about 150 mA by resistors R7 and R8 (which are about 10k ohm) and capacitor C3 blocks any overall DC component. The output frequency will vary slightly with the battery voltage, but the variation is quite small, typically, preferred frequency setting of 50 $H_z$, it will be from 52 to 48 $H_z$ for a voltage drop of from 3.2 to 2.2 volts.

The toothbrush head 18 may be replaceable. A removable cover may be provided on the handle for replacement of the battery. LED1 will not flash when the battery is discharged.

In use, the switch 30 is pressed which actuates the timer circuit which in turn activates the indicator circuit 44 to flash the LED1 on and off and provide a bipolar signal at the electrodes 22, 40. A hand gripping the handle 14 will make contact with the electrode 40, whilst the electrode 22 will make electrical contact with the gums and teeth via toothpaste, saliva etc. in the mouth.

By using an A.C. or bipolar signal with a 50 percent duty cycle, for example alternate 10 millisecond positive and negative pulses, any risk of electrodeposition is minimised. However, in some circumstances it may be desirable to have an overall DC current which may be particularly beneficial. This could be achieved by altering the relative duty cycles of the positive and negative pulses to say 25:75. A particularly preferred duty cycle is 5:95. Also it may be desirable to have a pulsed bipolar waveform, the pulses preferably being, for example, about 50 microseconds at a frequency of 50 $H_z$.

FIGS. 6 and 7 show a second embodiment of a toothbrush in accordance with the invention.

The toothbrush 60 comprises a main body portion 62 which is moulded from plastics material. The body portion 62 comprises handle portion 64, a neck 65 and a head portion 66. The handle portion 64 has a compartment 68 which houses electronic circuitry (not shown) and a battery 70. The compartment 68 is closed by an electrically conductive cover 72 which forms first electrode 40 (FIG. 5).

Bristles 74 of the toothbrush are held in a plastic slider 76 which is slidably mounted in the head portion 66 by means of a dovetail connection 78. The slider 76 is a tight fit in the head portion and a detent or the like may be provided to prevent the slider 76 coming loose when cleaning the teeth.

The first electrode 22 of the toothbrush is formed in two parts. A first electrode part (not shown) is insert moulded in the neck 65 and extends between the compartment 68 where it connects with the electronic circuitry, and the head portion 66 where it connects with the second electrode part 22a. Electrode part 22a has nibs (not shown) similar to nibs 24 in the embodiment of FIGS. 1 to 4.

A switch 80 and an LED indicator 82 are provided on the convex side of the junction between the body portion 64 and neck 65.

Figure 8:
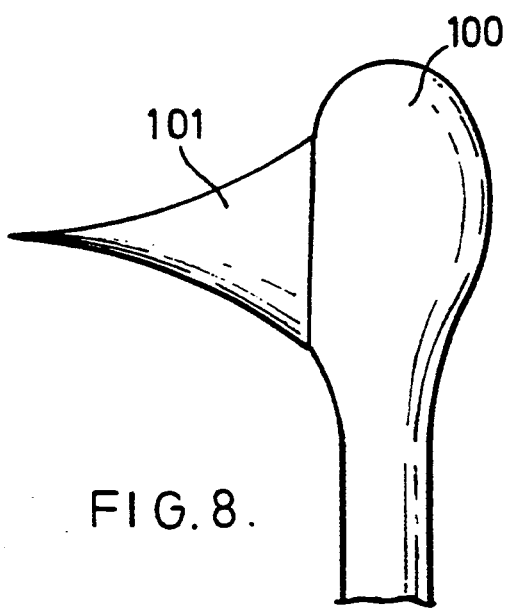
FIG. 8 is a side view of part one form of tooth pick forming a third embodiment of the invention.

In FIG. 8, a tooth pick comprises a head portion 100 within which a first electrode (not shown) is mounted in electrical contact with a base of a pointed conductive rubber finger 101. A second electrode is mounted as in the toothbrushes described above, in a handle of the tooth pick to contact the hand of a user. The second electrode could also be mounted the outer surface of the body to make contact with the mouth of a user. The body of the tooth pick incorporates the necessary circuit as described earlier and a battery power pack, or is provided with a lead to connect to a suitable mains powered supply, so that the finger 101 can apply fluctuating electrical signals to the gingival region of the mouth.

Figure 9:
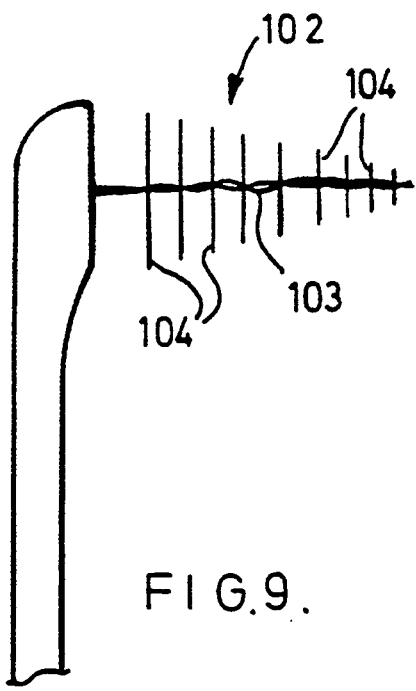
FIG. 9 is a side view of part of another form of tooth pick forming a fourth embodiment of the invention.

In FIG. 9, a similar arrangement is shown but a finger 102 consists of twisted and electrically conductive wires 103 entrapping circular arrays of bristles 104 to form a pointed brush arrangement. Such pointed brush arrangements are known per se. The electrical signals are provided, as described above, via circuitry in the handle of the tooth pick, and applied to the wires 103.

Figure 10:
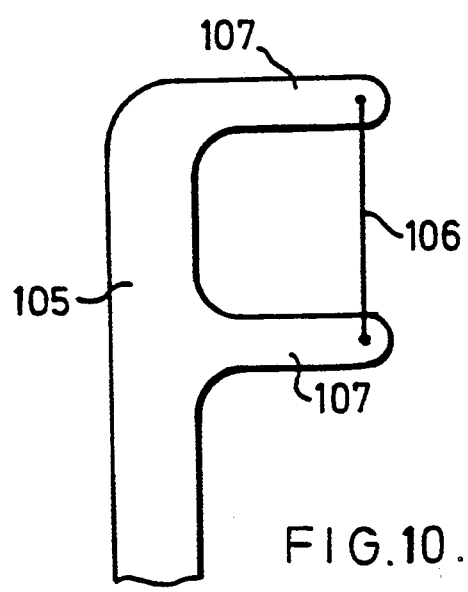
FIG. 10 is a side view of part of a floss holder forming a fifth embodiment of the invention.
Figure 11:
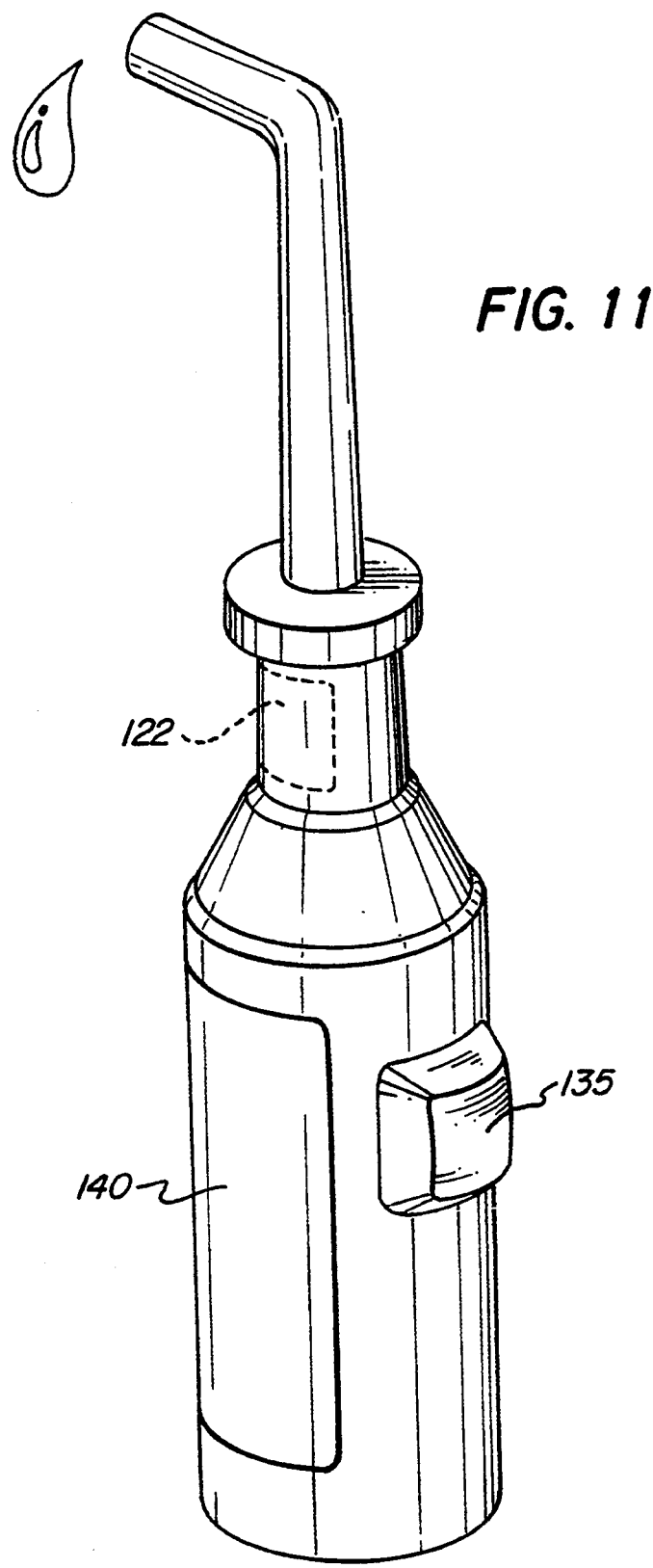
FIG. 11 is a perspective view of a water pick according to the invention.

In FIG. 10, the dental aid is in the form of a so-called "floss holder". Normally such arrangements are provided so that a dental floss strand can be selectively used to clean between teeth. The floss holder in FIG. 10 has a head 105 and length of thread 106 extending between limbs 107. The thread 106 is normally electrically non-conductive, but may be made wholly or partially conductive, and is used to penetrate between the teeth and to be moved adjacent the gingival regions of the mouth. A body (not shown) attached to the head contains, in a manner described above, the electrical circuitry for generating the electrical signals as required.

The dental aid may also take the form of a water pick. Water picks are known per se and consist of a body having a pointed outlet nozzle supplied with and arranged to direct a stream of water under pressure to chosen regions of the mouth. Normally, water picks are used for cleaning the gums around the base of each tooth. In accordance with the present invention, a water pick is provided in which the body contains electrical circuitry, which is battery powered from within the body or supplied with power via a suitable lead from a mains supply. The water pick of the present invention is arranged to provide the fluctuating electrical signal to the exiting water jet so that the signal is applied in use via the jet as required to the gingival regions of the mouth.

The embodiments of FIGS. 8,9 and 10 may be arranged with detached head portions and the floss holder of FIG. 10 may be arranged so that the thread 106 is readily replacable.

Various modifications may be made to the described embodiment and it is desired to include all such modifications as fall within the scope of the accompanying claims.

I claim:

1. A battery-operated dental cleaning device comprising means to apply non-symmetrical bi-polar electrical signals having a square or sawtooth waveform to the gingival region of the mouth, such that there is an overall DC component in the electrical signals.

2. A dental cleaning device according to claim 1, in which the signals have a voltage of about 3 volts.

3. A dental cleaning device according to claim 1, in which the signals have a frequency in the range 30 to 70 $H_z$.

4. A dental cleaning device according to claim 1, in which the signals each have a duty cycle of 25:75.

5. A dental cleaning device according to claim 1, in which the signals each have a duty cycle of 5:95.

6. A dental cleaning device as claimed in claim 1, in which the dental aid comprises a tooth brush having a head portion carrying a brush for brushing the teeth, and a first electrode mounted on the head portion for making electrical contact with the gingival region.

7. A dental cleaning device as claimed in claim 6 and comprising a tooth brush, in which the brush comprises a plurality of bristles mounted at one end in the head, and the first electrode mounted in the head portion, wherein the electrode is surrounded by the bristles so as to avoid physical contact with the mouth.

8. A dental cleaning device as claimed in claim 6 having a handle portion and a second electrode mounted on the handle portion for making electrical contact with the hand.

9. A dental cleaning device as claimed in claim 1, including a tooth brush having a body portion, a neck portion which extends at an angle of about +160 to +170 degrees to the body portion, and a head portion which extends at an angle of about −145 to −170 degrees to the neck portion.

10. A dental cleaning device according to claim 1, said device being in the form of a tooth pick.

11. A dental cleaning device according to claim 1, said device being in the form of a floss holder.

12. A dental cleaning device according to claim 1, said device being in the form of a water pick.

13. A self-contained, hand-held, battery-operated dental cleaning device capable of applying bi-polar electrical signals to the gingival region of the mouth, said signals being of a regular sinusoidal, square or sawtooth waveform, comprising:

an elongated housing comprising two opposed ends and an enclosed interior compartment, wherein one of said ends is adapted for grasping by hand and the other end is adapted for placing in the mouth;

signal generating means within the interior compartment for generating bi-polar electrical signals for transmission to a pair of electrodes, said signal generating means comprising a battery, a timer circuit, a waveform generator, and a switch operable to connect and interrupt flow of current from said battery to said timer circuit, said signal generating means being capable of providing a relative duty cycle providing an overall DC current; and a pair of electrodes, one of said electrodes being positioned at said end adapted for grasping by hand and the other on said end adapted for placing in the mouth, said electrodes capable of delivering said bi-polar electrical signals to the mouth.

* * * * *